(12) United States Patent
Videbaek

(10) Patent No.: US 8,708,930 B2
(45) Date of Patent: *Apr. 29, 2014

(54) BIOPSY APPARATUS HAVING INTEGRATED FLUID MANAGEMENT

(71) Applicant: Bard Peripheral Vascular, Inc., Tempe, AZ (US)

(72) Inventor: Karsten Videbaek, Jyllinge (DK)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/798,336

(22) Filed: Mar. 13, 2013

(65) Prior Publication Data

US 2013/0197391 A1 Aug. 1, 2013

Related U.S. Application Data

(63) Continuation of application No. 13/259,494, filed as application No. PCT/US2009/040663 on Apr. 15, 2009.

(51) Int. Cl.
*A61B 10/00* (2006.01)
*B65D 81/00* (2006.01)
*B01D 35/30* (2006.01)

(52) U.S. Cl.
USPC ........... 600/562; 600/564; 600/565; 600/566; 600/567; 600/568; 600/573; 600/575; 210/232

(58) Field of Classification Search
USPC ......... 600/562, 564, 565, 566, 567, 568, 573, 600/575; 210/232
See application file for complete search history.

(56) References Cited

U.S. PATENT DOCUMENTS

| 737,293 A | 8/1903 | Summerfeldt |
| 1,585,934 A | 5/1926 | Muir |

(Continued)

FOREIGN PATENT DOCUMENTS

| CN | 101011268 A | 8/2007 |
| CN | 101032420 A | 9/2007 |

(Continued)

OTHER PUBLICATIONS

MAXIM; Maxim8606; USB/AC Adapter, Li+ Linear Battery Charger with Integrated 50m Omega Battery Switch in TDFN; http://datasheets.maxim-ic.com/en/ds/MAX8606.pdf; Dec. 2008; Rev 1.

*Primary Examiner* — Rene Towa
*Assistant Examiner* — May Abouelela

(57) ABSTRACT

A biopsy apparatus includes a driver assembly and a disposable biopsy probe assembly for releasable attachment to the driver assembly. The driver assembly includes a first vacuum path having a first one-way valve configured and arranged to permit a negative pressure fluid flow toward a vacuum source and to prevent a positive pressure fluid flow away from the vacuum source. The disposable biopsy probe assembly includes a second vacuum path having a second one-way valve configured and arranged to permit the negative pressure fluid flow from a sample basket and to redundantly prevent the positive pressure fluid flow toward the sample basket. A fluid management tank is fluidically interposed in the second vacuum path between the first end and the second end. The fluid management tank includes a filter arrangement to prevent a flow of residual biopsy biological material from the sample basket to the vacuum source.

8 Claims, 6 Drawing Sheets

(56) References Cited

U.S. PATENT DOCUMENTS

| | | | |
|---|---|---|---|
| 1,663,761 A | 3/1928 | Johnson | |
| 2,953,934 A | 9/1960 | Sundt | |
| 3,019,733 A | 2/1962 | Braid | |
| 3,224,434 A * | 12/1965 | Molomut et al. | 600/562 |
| 3,289,669 A | 12/1966 | Dwyer et al. | |
| 3,477,423 A | 11/1969 | Griffith | |
| 3,512,519 A | 5/1970 | Hall | |
| 3,561,429 A | 2/1971 | Jewett et al. | |
| 3,565,074 A | 2/1971 | Foti | |
| 3,606,878 A | 9/1971 | Kellogg | |
| 3,727,602 A | 4/1973 | Hyden et al. | |
| 3,732,858 A | 5/1973 | Banko | |
| 3,785,380 A | 1/1974 | Brumfield | |
| 3,800,783 A | 4/1974 | Jamshidi | |
| 3,844,272 A | 10/1974 | Banko | |
| 3,882,849 A | 5/1975 | Jamshidi | |
| 3,889,682 A * | 6/1975 | Denis et al. | 604/119 |
| 4,275,730 A | 6/1981 | Hussein | |
| 4,282,884 A | 8/1981 | Boebel | |
| 4,306,570 A | 12/1981 | Matthews | |
| 4,354,092 A | 10/1982 | Manabe et al. | |
| 4,393,879 A * | 7/1983 | Milgrom | 600/571 |
| 4,445,509 A | 5/1984 | Auth | |
| 4,490,137 A | 12/1984 | Moukheibir | |
| 4,549,554 A | 10/1985 | Markham | |
| 4,577,629 A | 3/1986 | Martinez | |
| 4,589,414 A | 5/1986 | Yoshida et al. | |
| 4,603,694 A | 8/1986 | Wheeler | |
| 4,605,011 A | 8/1986 | Naslund | |
| 4,616,215 A | 10/1986 | Maddalena | |
| 4,617,430 A | 10/1986 | Bryant | |
| 4,620,539 A | 11/1986 | Andrews et al. | |
| 4,643,197 A | 2/1987 | Greene et al. | |
| 4,645,153 A | 2/1987 | Granzow et al. | |
| 4,678,459 A | 7/1987 | Onik et al. | |
| 4,696,298 A | 9/1987 | Higgins et al. | |
| 4,702,260 A | 10/1987 | Wang | |
| 4,706,687 A | 11/1987 | Rogers | |
| 4,776,346 A | 10/1988 | Beraha et al. | |
| 4,792,327 A | 12/1988 | Swartz | |
| 4,844,087 A | 7/1989 | Garg | |
| 4,850,354 A | 7/1989 | McGurk-Burleson et al. | |
| 4,893,635 A | 1/1990 | de Groot et al. | |
| 4,907,598 A | 3/1990 | Bauer | |
| RE33,258 E | 7/1990 | Onik et al. | |
| 4,940,061 A | 7/1990 | Terwilliger et al. | |
| 4,952,817 A | 8/1990 | Bolan et al. | |
| 4,958,625 A | 9/1990 | Bates et al. | |
| 4,967,762 A | 11/1990 | DeVries | |
| 4,986,278 A | 1/1991 | Ravid et al. | |
| 4,986,279 A | 1/1991 | O'Neill | |
| 4,986,807 A | 1/1991 | Farr | |
| 4,989,614 A | 2/1991 | Dejter, Jr. et al. | |
| 5,025,797 A | 6/1991 | Baran | |
| 5,048,538 A | 9/1991 | Terwilliger et al. | |
| 5,057,822 A | 10/1991 | Hoffman | |
| 5,078,603 A * | 1/1992 | Cohen | 433/91 |
| 5,125,413 A | 6/1992 | Baran | |
| 5,138,245 A | 8/1992 | Mattinger et al. | |
| 5,146,921 A | 9/1992 | Terwilliger et al. | |
| 5,158,528 A | 10/1992 | Walker et al. | |
| 5,176,628 A | 1/1993 | Charles et al. | |
| 5,223,012 A * | 6/1993 | Best et al. | 55/523 |
| 5,225,763 A | 7/1993 | Krohn et al. | |
| 5,234,000 A | 8/1993 | Hakky et al. | |
| 5,236,334 A | 8/1993 | Bennett | |
| 5,242,404 A | 9/1993 | Conley et al. | |
| 5,249,583 A | 10/1993 | Mallaby | |
| 5,282,476 A | 2/1994 | Terwilliger | |
| 5,282,477 A | 2/1994 | Bauer | |
| 5,290,253 A * | 3/1994 | Kira | 604/190 |
| 5,324,306 A | 6/1994 | Makower et al. | |
| 5,334,183 A | 8/1994 | Wuchinich | |
| 5,368,029 A | 11/1994 | Holcombe et al. | |
| 5,368,045 A | 11/1994 | Clement et al. | |
| 5,383,874 A | 1/1995 | Jackson et al. | |
| 5,397,462 A * | 3/1995 | Higashijima et al. | 210/136 |
| 5,400,798 A | 3/1995 | Baran | |
| 5,439,474 A | 8/1995 | Li | |
| 5,458,112 A | 10/1995 | Weaver | |
| 5,469,860 A | 11/1995 | De Santis | |
| 5,471,994 A | 12/1995 | Guirguis | |
| 5,479,486 A | 12/1995 | Saji | |
| 5,485,917 A | 1/1996 | Early | |
| 5,492,130 A | 2/1996 | Chiou | |
| 5,511,556 A | 4/1996 | DeSantis | |
| 5,526,822 A | 6/1996 | Burbank et al. | |
| 5,535,755 A | 7/1996 | Heske | |
| 5,546,957 A | 8/1996 | Heske | |
| 5,554,151 A | 9/1996 | Hinchliffe | |
| 5,560,373 A | 10/1996 | De Santis | |
| 5,564,436 A | 10/1996 | Hakky et al. | |
| 5,569,284 A | 10/1996 | Young et al. | |
| 5,575,293 A | 11/1996 | Miller et al. | |
| 5,591,170 A | 1/1997 | Spievack et al. | |
| 5,601,585 A | 2/1997 | Banik et al. | |
| 5,602,449 A | 2/1997 | Krause et al. | |
| 5,617,874 A | 4/1997 | Baran | |
| 5,649,547 A | 7/1997 | Ritchart et al. | |
| 5,655,542 A | 8/1997 | Weilandt | |
| 5,655,657 A | 8/1997 | Roshdy | |
| 5,665,101 A | 9/1997 | Becker et al. | |
| 5,669,394 A | 9/1997 | Bergey et al. | |
| 5,699,909 A | 12/1997 | Foster | |
| 5,700,265 A | 12/1997 | Romano | |
| 5,709,697 A | 1/1998 | Ratcliff et al. | |
| 5,720,760 A | 2/1998 | Becker et al. | |
| 5,735,264 A | 4/1998 | Siczek et al. | |
| 5,752,923 A | 5/1998 | Terwilliger | |
| 5,755,714 A | 5/1998 | Murphy-Chutorian | |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,779,649 A * | 7/1998 | Herbert | 600/571 |
| 5,788,651 A | 8/1998 | Weilandt | |
| 5,792,167 A | 8/1998 | Kablik et al. | |
| 5,807,282 A | 9/1998 | Fowler | |
| 5,817,033 A | 10/1998 | DeSantis et al. | |
| 5,817,034 A | 10/1998 | Milliman et al. | |
| 5,823,970 A | 10/1998 | Terwilliger | |
| 5,827,305 A | 10/1998 | Gordon | |
| 5,830,219 A | 11/1998 | Bird et al. | |
| D403,405 S | 12/1998 | Terwilliger | |
| 5,857,982 A | 1/1999 | Milliman et al. | |
| 5,879,365 A | 3/1999 | Whitfield et al. | |
| 5,908,233 A | 6/1999 | Heskett et al. | |
| 5,913,857 A | 6/1999 | Ritchart et al. | |
| 5,916,198 A | 6/1999 | Dillow | |
| 5,916,229 A | 6/1999 | Evans | |
| 5,928,164 A | 7/1999 | Burbank et al. | |
| 5,944,673 A | 8/1999 | Gregoire et al. | |
| 5,951,490 A | 9/1999 | Fowler | |
| 5,951,575 A | 9/1999 | Bolduc et al. | |
| 5,964,716 A | 10/1999 | Gregoire et al. | |
| 5,971,939 A | 10/1999 | DeSantis et al. | |
| 5,976,164 A | 11/1999 | Bencini et al. | |
| 5,980,469 A | 11/1999 | Burbank et al. | |
| 5,980,545 A | 11/1999 | Pacala et al. | |
| 6,007,495 A | 12/1999 | Matula | |
| 6,007,497 A * | 12/1999 | Huitema | 600/567 |
| 6,007,556 A | 12/1999 | Kablik et al. | |
| 6,017,316 A | 1/2000 | Ritchart et al. | |
| 6,018,227 A | 1/2000 | Kumar et al. | |
| 6,019,733 A | 2/2000 | Farascioni | |
| 6,022,324 A | 2/2000 | Skinner | |
| 6,022,325 A | 2/2000 | Siczek et al. | |
| 6,027,458 A | 2/2000 | Janssens | |
| 6,036,657 A | 3/2000 | Milliman et al. | |
| 6,050,955 A | 4/2000 | Bryan et al. | |
| 6,055,870 A | 5/2000 | Jaeger | |
| 6,071,247 A * | 6/2000 | Kennedy | 600/562 |
| 6,077,230 A | 6/2000 | Gregoire et al. | |
| 6,083,176 A | 7/2000 | Terwilliger | |

(56) References Cited

U.S. PATENT DOCUMENTS

| | | | |
|---|---|---|---|
| 6,083,237 A | 7/2000 | Huitema et al. | |
| 6,086,544 A * | 7/2000 | Hibner et al. | 600/568 |
| 6,106,484 A | 8/2000 | Terwilliger | |
| 6,110,129 A | 8/2000 | Terwilliger | |
| 6,120,462 A | 9/2000 | Hibner et al. | |
| 6,123,957 A | 9/2000 | Jernberg | |
| 6,126,617 A | 10/2000 | Weilandt et al. | |
| 6,142,955 A | 11/2000 | Farascioni et al. | |
| 6,162,187 A | 12/2000 | Buzzard et al. | |
| 6,165,136 A | 12/2000 | Nishtala | |
| 6,193,673 B1 | 2/2001 | Viola et al. | |
| 6,196,978 B1 | 3/2001 | Weilandt et al. | |
| 6,213,957 B1 | 4/2001 | Milliman et al. | |
| 6,220,248 B1 | 4/2001 | Voegele et al. | |
| 6,231,522 B1 | 5/2001 | Voegele et al. | |
| 6,241,687 B1 | 6/2001 | Voegele et al. | |
| 6,267,759 B1 | 7/2001 | Quick | |
| 6,273,861 B1 | 8/2001 | Bates et al. | |
| 6,273,862 B1 * | 8/2001 | Privitera et al. | 600/568 |
| 6,280,398 B1 | 8/2001 | Ritchart et al. | |
| 6,283,925 B1 | 9/2001 | Terwilliger | |
| 6,322,523 B2 | 11/2001 | Weilandt et al. | |
| 6,328,701 B1 | 12/2001 | Terwilliger | |
| 6,331,166 B1 | 12/2001 | Burbank et al. | |
| 6,358,217 B1 | 3/2002 | Bourassa | |
| 6,402,701 B1 | 6/2002 | Kaplan et al. | |
| 6,419,641 B1 | 7/2002 | Mark et al. | |
| 6,428,486 B2 | 8/2002 | Ritchart et al. | |
| 6,428,487 B1 * | 8/2002 | Burdorff et al. | 600/568 |
| 6,432,064 B1 | 8/2002 | Hibner et al. | |
| 6,432,065 B1 * | 8/2002 | Burdorff et al. | 600/566 |
| 6,434,507 B1 | 8/2002 | Clayton et al. | |
| 6,436,054 B1 | 8/2002 | Viola et al. | |
| 6,461,302 B1 | 10/2002 | Thompson | |
| 6,471,659 B2 | 10/2002 | Eggers et al. | |
| 6,482,158 B2 | 11/2002 | Mault | |
| 6,485,436 B1 | 11/2002 | Truckai et al. | |
| 6,488,636 B2 | 12/2002 | Bryan et al. | |
| 6,527,736 B1 | 3/2003 | Attinger et al. | |
| 6,540,694 B1 | 4/2003 | Van Bladel et al. | |
| 6,540,761 B2 | 4/2003 | Houser | |
| 6,544,194 B1 | 4/2003 | Kortenbach et al. | |
| 6,551,255 B2 | 4/2003 | Van Bladel et al. | |
| 6,554,779 B2 | 4/2003 | Viola et al. | |
| 6,585,664 B2 * | 7/2003 | Burdorff et al. | 600/564 |
| 6,585,694 B1 | 7/2003 | Smith et al. | |
| 6,586,585 B1 * | 7/2003 | Bastian | 536/25.4 |
| 6,638,235 B2 * | 10/2003 | Miller et al. | 600/566 |
| 6,656,133 B2 | 12/2003 | Voegele et al. | |
| 6,659,105 B2 | 12/2003 | Burbank et al. | |
| 6,659,338 B1 | 12/2003 | Dittmann et al. | |
| 6,683,439 B2 | 1/2004 | Takano et al. | |
| 6,689,072 B2 * | 2/2004 | Kaplan et al. | 600/567 |
| 6,695,786 B2 | 2/2004 | Wang et al. | |
| 6,702,832 B2 * | 3/2004 | Ross et al. | 606/166 |
| 6,712,773 B1 | 3/2004 | Viola | |
| 6,712,774 B2 | 3/2004 | Voegele et al. | |
| 6,752,768 B2 * | 6/2004 | Burdorff et al. | 600/568 |
| 6,753,671 B1 | 6/2004 | Harvey | |
| 6,755,802 B2 * | 6/2004 | Bell | 604/6.15 |
| 6,758,824 B1 | 7/2004 | Miller et al. | |
| 6,764,495 B2 | 7/2004 | Lee et al. | |
| 6,832,990 B2 | 12/2004 | Kortenbach et al. | |
| 6,849,080 B2 | 2/2005 | Lee et al. | |
| 6,860,860 B2 | 3/2005 | Viola | |
| 6,887,210 B2 | 5/2005 | Quay | |
| 6,908,440 B2 | 6/2005 | Fisher | |
| D508,458 S | 8/2005 | Solland et al. | |
| 6,926,676 B2 | 8/2005 | Turturro et al. | |
| 6,984,213 B2 | 1/2006 | Horner et al. | |
| 7,004,174 B2 * | 2/2006 | Eggers et al. | 128/898 |
| 7,010,332 B1 | 3/2006 | Irvin et al. | |
| 7,025,732 B2 * | 4/2006 | Thompson et al. | 600/564 |
| D525,583 S | 7/2006 | Vu | |
| 7,153,274 B2 | 12/2006 | Stephens et al. | |
| 7,156,814 B1 * | 1/2007 | Williamson et al. | 600/562 |
| 7,182,754 B2 | 2/2007 | Brigham et al. | |
| 7,189,206 B2 | 3/2007 | Quick et al. | |
| 7,189,207 B2 | 3/2007 | Viola | |
| 7,219,867 B2 | 5/2007 | Kalis et al. | |
| 7,226,424 B2 | 6/2007 | Ritchart et al. | |
| 7,252,641 B2 | 8/2007 | Thompson et al. | |
| 7,276,032 B2 | 10/2007 | Hibner | |
| 7,328,794 B2 | 2/2008 | Lubs et al. | |
| 7,347,828 B2 | 3/2008 | Francese et al. | |
| 7,347,829 B2 | 3/2008 | Mark et al. | |
| 7,374,544 B2 | 5/2008 | Freeman et al. | |
| 7,390,306 B2 | 6/2008 | Mark | |
| 7,397,654 B2 | 7/2008 | Mori | |
| 7,402,140 B2 | 7/2008 | Spero et al. | |
| 7,405,536 B2 | 7/2008 | Watts | |
| 7,407,054 B2 | 8/2008 | Seiler et al. | |
| 7,432,813 B2 | 10/2008 | Postma | |
| 7,452,367 B2 | 11/2008 | Rassman et al. | |
| 7,458,940 B2 * | 12/2008 | Miller | 600/568 |
| 7,464,040 B2 | 12/2008 | Joao | |
| 7,473,232 B2 | 1/2009 | Teague | |
| 7,481,775 B2 | 1/2009 | Weikel, Jr. et al. | |
| 7,490,048 B2 | 2/2009 | Joao | |
| 7,491,177 B2 | 2/2009 | Hibner | |
| 7,494,473 B2 * | 2/2009 | Eggers et al. | 600/582 |
| 7,497,833 B2 | 3/2009 | Miller | |
| 7,510,534 B2 * | 3/2009 | Burdorff et al. | 600/564 |
| 7,513,877 B2 | 4/2009 | Viola | |
| 7,517,321 B2 * | 4/2009 | McCullough et al. | 600/566 |
| 7,517,322 B2 | 4/2009 | Weikel, Jr. et al. | |
| 7,549,978 B2 * | 6/2009 | Carlson et al. | 604/156 |
| 7,575,557 B2 | 8/2009 | Morton et al. | |
| 7,648,466 B2 | 1/2010 | Stephens et al. | |
| 7,670,299 B2 | 3/2010 | Beckman et al. | |
| 7,717,861 B2 | 5/2010 | Weikel et al. | |
| 7,727,164 B2 | 6/2010 | Cicenas et al. | |
| 7,740,594 B2 | 6/2010 | Hibner | |
| 7,740,596 B2 | 6/2010 | Hibner | |
| 7,740,597 B2 | 6/2010 | Cicenas et al. | |
| 7,758,515 B2 * | 7/2010 | Hibner | 600/566 |
| 7,762,961 B2 | 7/2010 | Heske et al. | |
| 7,806,834 B2 | 10/2010 | Beckman et al. | |
| 7,828,746 B2 | 11/2010 | Teague | |
| 7,846,109 B2 | 12/2010 | Parihar et al. | |
| 7,854,706 B2 * | 12/2010 | Hibner | 600/566 |
| 7,862,517 B2 | 1/2011 | Tsonton et al. | |
| 7,862,518 B2 | 1/2011 | Parihar | |
| 7,871,384 B2 * | 1/2011 | Thompson et al. | 600/568 |
| 7,883,476 B2 | 2/2011 | Miller et al. | |
| 7,883,494 B2 | 2/2011 | Martin | |
| 7,906,076 B2 * | 3/2011 | Fischer | 422/536 |
| 7,914,462 B2 * | 3/2011 | Hutchins et al. | 600/562 |
| 7,959,580 B2 * | 6/2011 | McCullough et al. | 600/566 |
| 7,974,681 B2 | 7/2011 | Wallace et al. | |
| 8,002,713 B2 | 8/2011 | Heske et al. | |
| 8,012,102 B2 * | 9/2011 | McCullough et al. | 600/566 |
| 8,016,844 B2 * | 9/2011 | Privitera et al. | 606/167 |
| 8,052,615 B2 | 11/2011 | Reuber et al. | |
| 8,057,402 B2 * | 11/2011 | Hibner et al. | 600/566 |
| 8,073,008 B2 | 12/2011 | Mehta et al. | |
| 8,075,495 B2 * | 12/2011 | Andreyko et al. | 600/567 |
| 8,083,687 B2 | 12/2011 | Parihar | |
| 8,109,885 B2 | 2/2012 | Heske et al. | |
| 8,118,755 B2 * | 2/2012 | Hibner et al. | 600/565 |
| 8,152,738 B2 * | 4/2012 | Li et al. | 600/566 |
| 8,162,850 B2 * | 4/2012 | Parihar et al. | 600/565 |
| 8,172,771 B2 * | 5/2012 | Miller et al. | 600/562 |
| 8,187,204 B2 * | 5/2012 | Miller et al. | 600/567 |
| 8,190,238 B2 | 5/2012 | Moll et al. | |
| 8,206,409 B2 * | 6/2012 | Privitera et al. | 606/167 |
| 8,251,916 B2 * | 8/2012 | Speeg et al. | 600/565 |
| 8,277,393 B2 * | 10/2012 | Miller et al. | 600/567 |
| 8,282,574 B2 * | 10/2012 | Coonahan et al. | 600/564 |
| 8,287,465 B2 * | 10/2012 | Hardin et al. | 600/565 |
| 8,313,444 B2 | 11/2012 | Thompson et al. | |
| 8,343,069 B2 * | 1/2013 | Uchiyama et al. | 600/562 |
| 8,430,825 B2 * | 4/2013 | Mark | 600/564 |
| 2001/0007925 A1 | 7/2001 | Ritchart et al. | |

(56) References Cited

U.S. PATENT DOCUMENTS

| | | |
|---|---|---|
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0029007 A1 | 3/2002 | Bryan et al. |
| 2002/0045839 A1* | 4/2002 | Voegele et al. ............... 600/564 |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0115942 A1* | 8/2002 | Stanford et al. ............... 600/562 |
| 2002/0120212 A1 | 8/2002 | Ritchart et al. |
| 2002/0143269 A1 | 10/2002 | Neuenfeldt |
| 2002/0156395 A1 | 10/2002 | Stephens et al. |
| 2003/0023188 A1 | 1/2003 | Kritzman et al. |
| 2003/0023239 A1 | 1/2003 | Burbank et al. |
| 2003/0093103 A1 | 5/2003 | Malackowski et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1 | 2/2004 | Privitera et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0167428 A1 | 8/2004 | Quick et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1* | 11/2004 | Merkle ............... 600/575 |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0054947 A1 | 3/2005 | Goldenberg |
| 2005/0065453 A1 | 3/2005 | Shabaz et al. |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1* | 6/2005 | Eggers et al. ............... 600/568 |
| 2005/0165329 A1 | 7/2005 | Taylor et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0275378 A1 | 12/2005 | Canino et al. |
| 2005/0277829 A1 | 12/2005 | Tsonton et al. |
| 2005/0277871 A1 | 12/2005 | Selis |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0129063 A1* | 6/2006 | Thompson et al. ............ 600/566 |
| 2006/0149162 A1 | 7/2006 | Daw et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2006/0260994 A1* | 11/2006 | Mark et al. ............... 210/232 |
| 2007/0016101 A1 | 1/2007 | Feldman et al. |
| 2007/0032741 A1 | 2/2007 | Hibner et al. |
| 2007/0032743 A1 | 2/2007 | Hibner |
| 2007/0055173 A1 | 3/2007 | DeLonzor et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0149894 A1* | 6/2007 | Heske et al. ............... 600/566 |
| 2007/0161925 A1 | 7/2007 | Quick et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179382 A1* | 8/2007 | Hibner ............... 600/567 |
| 2007/0213590 A1 | 9/2007 | Squicciarini |
| 2007/0213630 A1* | 9/2007 | Beckman et al. ............ 600/562 |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1* | 11/2007 | Hibner ............... 600/566 |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0292858 A1* | 12/2007 | Chen et al. ............... 435/6 |
| 2007/0293788 A1 | 12/2007 | Entrekin et al. |
| 2007/0293830 A1* | 12/2007 | Martin ............... 604/289 |
| 2008/0004545 A1 | 1/2008 | Garrison |
| 2008/0007217 A1 | 1/2008 | Riley |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0079391 A1 | 4/2008 | Schroeck et al. |
| 2008/0103411 A1 | 5/2008 | Van Bladel et al. |
| 2008/0110261 A1 | 5/2008 | Randall et al. |
| 2008/0125634 A1* | 5/2008 | Ryan et al. ............... 600/342 |
| 2008/0135443 A1 | 6/2008 | Frojd et al. |
| 2008/0146962 A1 | 6/2008 | Ritchie et al. |
| 2008/0146965 A1* | 6/2008 | Privitera et al. ............... 600/567 |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1* | 8/2008 | Speeg et al. ............... 604/326 |
| 2008/0200833 A1 | 8/2008 | Hardin et al. |
| 2008/0200836 A1* | 8/2008 | Speeg et al. ............... 600/567 |
| 2008/0208194 A1 | 8/2008 | Bickenbach |
| 2008/0208208 A1 | 8/2008 | Speeg et al. |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0082695 A1 | 3/2009 | Whitehead |
| 2009/0087249 A1* | 4/2009 | Flagle et al. ............... 403/31 |
| 2009/0088666 A1* | 4/2009 | Miller et al. ............... 600/568 |
| 2009/0112118 A1* | 4/2009 | Quick et al. ............... 600/564 |

(56) References Cited

U.S. PATENT DOCUMENTS

| | | | |
|---|---|---|---|
| 2009/0125062 A1 | 5/2009 | Arnin | |
| 2009/0137927 A1 | 5/2009 | Miller | |
| 2009/0171242 A1 | 7/2009 | Hibner | |
| 2009/0171243 A1* | 7/2009 | Hibner et al. | 600/566 |
| 2009/0204022 A1* | 8/2009 | Schwindt | 600/566 |
| 2009/0227893 A1 | 9/2009 | Coonahan et al. | |
| 2010/0030020 A1 | 2/2010 | Sanders et al. | |
| 2010/0030108 A1 | 2/2010 | Anderson et al. | |
| 2010/0063416 A1 | 3/2010 | Cicenas et al. | |
| 2010/0106053 A1 | 4/2010 | Videbaek et al. | |
| 2010/0152610 A1 | 6/2010 | Parihar et al. | |
| 2010/0152611 A1 | 6/2010 | Parihar et al. | |
| 2010/0160820 A1 | 6/2010 | Weikel, Jr. et al. | |
| 2010/0160823 A1 | 6/2010 | Parihar et al. | |
| 2010/0210966 A1* | 8/2010 | Videbæk | 600/564 |
| 2010/0234760 A1 | 9/2010 | Almazan | |
| 2010/0292607 A1 | 11/2010 | Moore et al. | |
| 2010/0312140 A1 | 12/2010 | Smith et al. | |
| 2010/0317995 A1 | 12/2010 | Hibner et al. | |
| 2010/0317997 A1 | 12/2010 | Hibner et al. | |
| 2010/0317998 A1 | 12/2010 | Hibner et al. | |
| 2010/0324449 A1 | 12/2010 | Rostaing et al. | |
| 2011/0004119 A1* | 1/2011 | Hoffa et al. | 600/566 |
| 2011/0054350 A1 | 3/2011 | Videbaek | |
| 2011/0077551 A1 | 3/2011 | Videbaek | |
| 2011/0087131 A1 | 4/2011 | Videbaek | |
| 2011/0105945 A1 | 5/2011 | Videbaek et al. | |
| 2011/0105946 A1 | 5/2011 | Sorensen et al. | |
| 2011/0152715 A1 | 6/2011 | Delap et al. | |
| 2011/0160611 A1 | 6/2011 | Ritchart et al. | |
| 2011/0224577 A1 | 9/2011 | Park | |
| 2012/0191009 A1 | 7/2012 | Hoon et al. | |
| 2012/0215130 A1 | 8/2012 | Field et al. | |

FOREIGN PATENT DOCUMENTS

| | | |
|---|---|---|
| DE | 3924291 A1 | 1/1991 |
| DE | 4041614 C1 | 10/1992 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| JP | 1-126957 A | 9/1987 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9628097 A1 | 9/1996 |
| WO | 9734531 A1 | 9/1997 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008040812 A1 | 4/2008 |
| WO | 2008131362 A2 | 10/2008 |
| WO | 2010107424 A1 | 9/2010 |
| WO | 2011019343 A1 | 2/2011 |

\* cited by examiner

BIOPSY APPARATUS HAVING INTEGRATED FLUID MANAGEMENT

CROSS REFERENCE TO RELATED APPLICATIONS

This application is a continuation of U.S. patent application Ser. No. 13/259,494 filed Sep. 23, 2011, which is a U.S. national phase of Interantional Application No. PCT/US2009/040663, filed Apr. 15, 2009, from which is priority is claimed and which is incorporated herein by reference in its entirety.

BACKGROUND OF THE INVENTION

1. Field of the Invention

The present invention relates to a biopsy apparatus, and, more particularly, to a biopsy apparatus having integrated fluid management.

2. Description of the Related Art

A biopsy may be performed on a patient to help in determining whether the cells in a biopsied region are cancerous. One biopsy technique used to evaluate breast tissue, for example, involves inserting a biopsy probe into the breast tissue region of interest to capture one or more tissue samples from the region. Such a biopsy technique often utilizes a vacuum to pull the tissue to be sampled into a sample notch of the biopsy probe, after which the tissue is severed and collected. One type of vacuum assisted biopsy apparatus includes a hand-held driver assembly having a vacuum source, and a disposable biopsy probe assembly configured for releasable attachment to the driver assembly. However, in the presence of the desired negative pressure generated by the vacuum source, residual biopsy biological material, e.g., blood and particulate matter, may be drawn into the vacuum path from the patient along with the tissue sample, and thus potentially contaminating the hand-held driver assembly. Also, in the event of an undesirable positive pressure arising in the vacuum path, the potential exists for a reverse flow of fluid in a direction from the hand-held driver assembly to the patient via the disposable biopsy probe assembly.

SUMMARY OF THE INVENTION

The present invention provides a fully integrated hand-held biopsy apparatus having fluid management to reduce the potential for a transfer of contaminants during a biopsy procedure.

As used herein, the terms "first" and "second" preceding an element name, e.g., first vacuum path, second vacuum path, etc., are for identification purposes to distinguish between different elements having similar characteristic, and are not intended to necessarily imply order, unless otherwise specified, nor are the terms "first" and "second" intended to preclude the inclusion of additional similar elements.

The invention in one form is directed to a biopsy apparatus. The biopsy apparatus includes a driver assembly configured to be grasped by a user and a disposable biopsy probe assembly configured for releasable attachment to the driver assembly. The driver assembly includes an electromechanical power source, a vacuum source, and a first vacuum path permanently associated with the vacuum source. The first vacuum path has a proximal end and a distal end, the proximal end being fixedly coupled to the vacuum source in fluid communication therewith. The first vacuum path has a first one-way valve configured and arranged to permit a negative pressure fluid flow toward the vacuum source and to prevent a positive pressure fluid flow away from the vacuum source toward the distal end. The disposable biopsy probe assembly includes a transmission device, a biopsy probe, and a second vacuum path. The transmission device is configured for driving engagement with the electromechanical power source. The biopsy probe is drivably coupled to the transmission device, and the biopsy probe has a sample basket for receiving a biopsy tissue sample. The second vacuum path has a first end and a second end, the first end being configured for removable attachment to the distal end of the first vacuum path and the second end being coupled in fluid communication with the sample basket. The second vacuum path has a second one-way valve configured and arranged to permit the negative pressure fluid flow from the sample basket and to redundantly prevent the positive pressure fluid flow from the first end of the second vacuum path toward the sample basket.

In some embodiments, for example, the disposable biopsy probe assembly may further include a fluid management tank fluidically interposed in the second vacuum path between the first end and the second end. The fluid management tank includes a body and a filter arrangement contained within the body. The filter arrangement is configured to prevent a flow of residual biopsy biological material from the sample basket to the vacuum source.

The invention in another form is directed to a fluid management system for use in a biopsy apparatus that utilizes a biopsy probe having a sample basket configured to receive a biopsy tissue sample. The fluid management system includes a vacuum source, a non-disposable vacuum path, and a disposable vacuum path. The non-disposable vacuum path has a proximal end and a distal end, the proximal end being fixedly coupled to the vacuum source in fluid communication therewith. The non-disposable vacuum path includes a first one-way valve configured and arranged to permit a negative pressure fluid flow toward the vacuum source and to prevent a positive pressure fluid flow away from the vacuum source toward the distal end of the non-disposable vacuum path. The disposable vacuum path is temporarily coupled in fluid communication with the vacuum source via the non-disposable vacuum path. The disposable vacuum path has a first end and a second end, the first end being configured for removable attachment to the distal end of the non-disposable vacuum path and the second end being coupled in fluid communication with the sample basket. The disposable vacuum path includes a second one-way valve configured and arranged to permit the negative pressure fluid flow toward the vacuum source from the sample basket and to redundantly prevent the positive pressure fluid flow away from the distal end of the non-disposable vacuum path toward the sample basket.

The invention in another form is directed to a disposable biopsy probe assembly configured for releasable attachment to a driver assembly having an electromechanical power source, a vacuum source, and a first vacuum path permanently associated with the vacuum source. The disposable biopsy probe assembly includes a transmission device, a biopsy probe, a second vacuum path, and a fluid management tank. The transmission device is configured for driving engagement with the electromechanical power source. The biopsy probe is drivably coupled to the transmission device. The biopsy probe has a sample basket for receiving a biopsy tissue sample. The second vacuum path has a first end and a second end, the first end being configured for removable attachment to the first vacuum path and the second end being coupled in fluid communication with the sample basket. The second vacuum path has a one-way valve configured and arranged to permit a negative pressure fluid flow from the sample basket and to prevent a positive pressure fluid flow from the first end of the second vacuum path toward the sample basket. A fluid management tank is fluidically interposed in the second vacuum path between the first end and the second end. The fluid management tank includes a body and a filter arrangement contained within the body configured to prevent a flow of residual biopsy biological material from the sample basket to the vacuum source with the negative pressure fluid flow. The filter arrangement includes a plurality of fluid absorption layers arranged side by side, each fluid absorption layer being spaced apart from an adjacent fluid absorption layer, and each fluid absorption layer having a respective through opening, wherein adjacent through openings of the plurality of fluid absorption layers are offset to form a tortuous open fluid passageway through the plurality of fluid absorption layers.

In accordance with one or more aspects of the invention, the fluid connection interface between the driver assembly and the disposable biopsy probe assembly is automatic upon installation of the disposable biopsy probe assembly on the driver assembly. Thus, no specific operator actions are required to establish the connection between the vacuum path of the disposable biopsy probe assembly and the vacuum source of the driver assembly.

Also, in accordance with one or more aspects of the invention, the biopsy apparatus is provided with multiple levels of prevention of cross-contamination between the non-invasive reusable driver assembly and the disposable biopsy probe assembly. In addition, there is provided multiple levels of prevention of reverse flow (positive pressure flow) from the vacuum source towards the patient. Also, the prevention of cross-contamination is facilitated by having on the disposable biopsy probe assembly a fluid management tank to provide fully enclosed storage of biopsy fluids with reduced risk of post-procedure spillage and multiple stages of absorption of biopsy liquids from vacuum pathway, as well as doing so while permitting 360-degree turnability of the biopsy apparatus without compromising vacuum pathways.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an embodiment of the invention, and such exemplifications are not to be construed as limiting the scope of the invention in any manner.

DETAILED DESCRIPTION OF THE INVENTION

Figure 1:
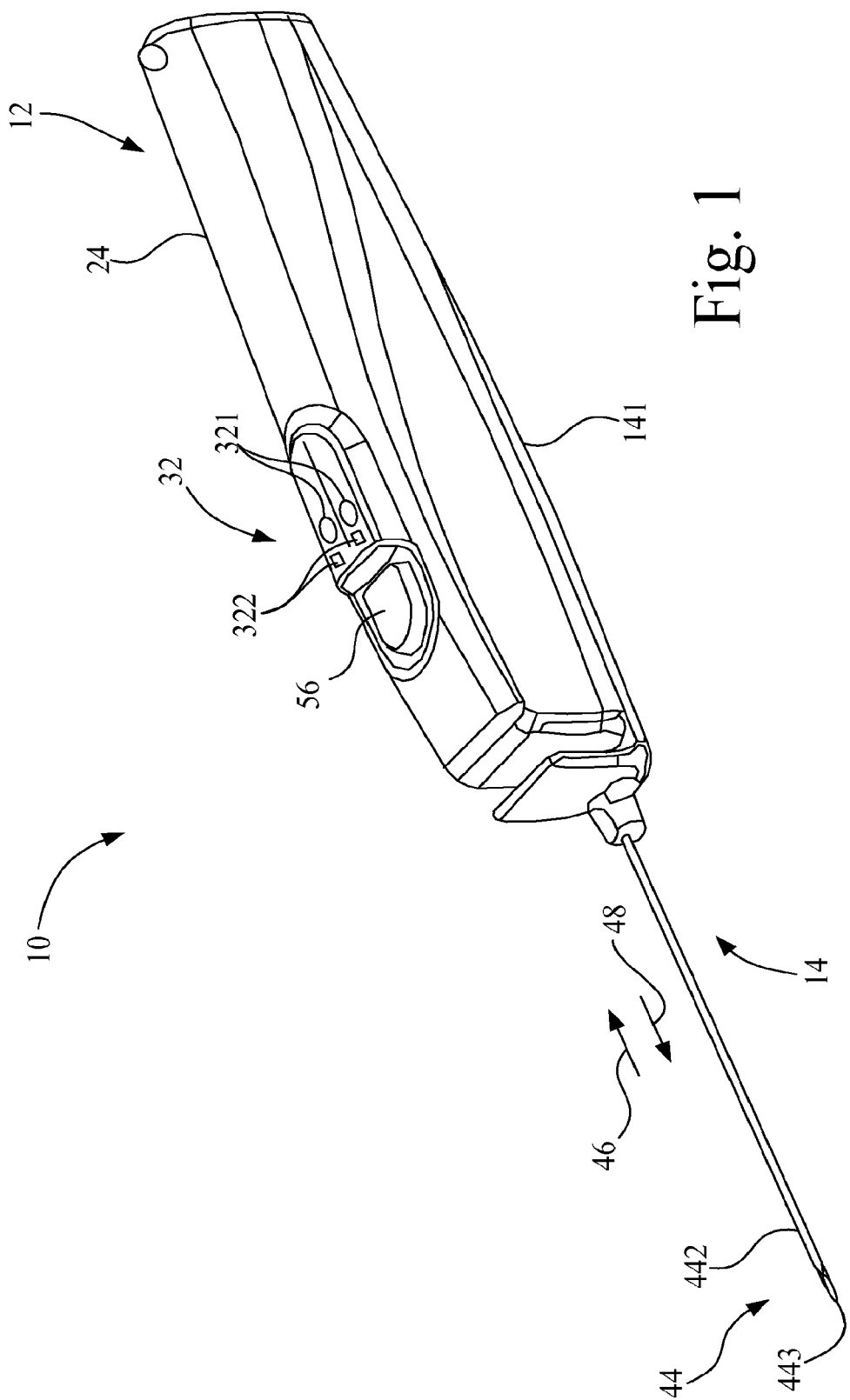
FIG. 1 is a perspective view of a biopsy apparatus, configured in accordance with an embodiment of the present invention, with a disposable biopsy probe mounted to a driver assembly.
Figure 2:
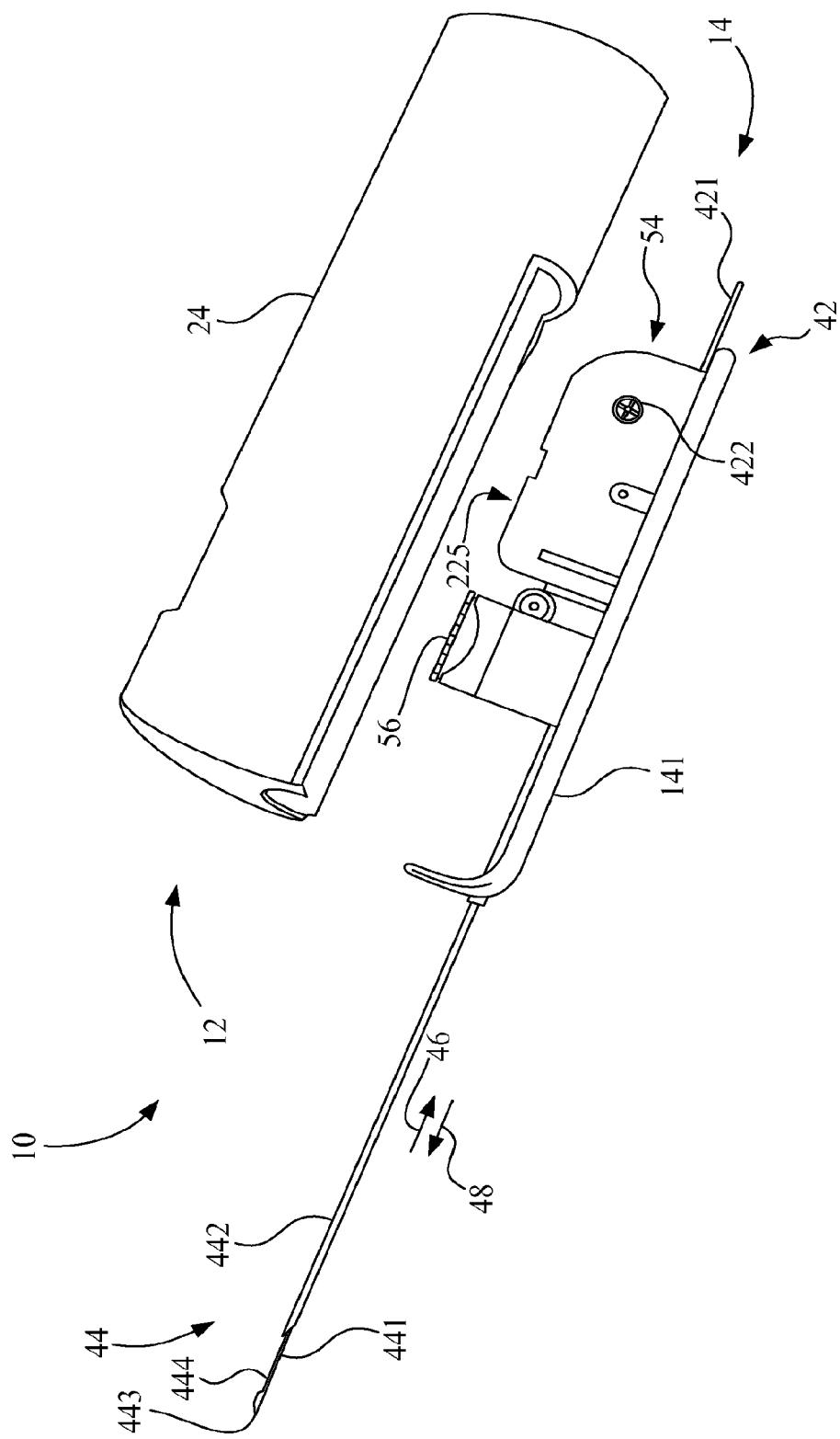
FIG. 2 is a perspective view of a biopsy apparatus of FIG. 1, with the disposable biopsy probe detached from the driver assembly.

Referring now to the drawings, and more particularly to FIGS. 1 and 2, there is shown a biopsy apparatus 10 which generally includes a non-invasive, e.g., non-disposable, driver assembly 12 and a disposable biopsy probe assembly 14.

Figure 3:
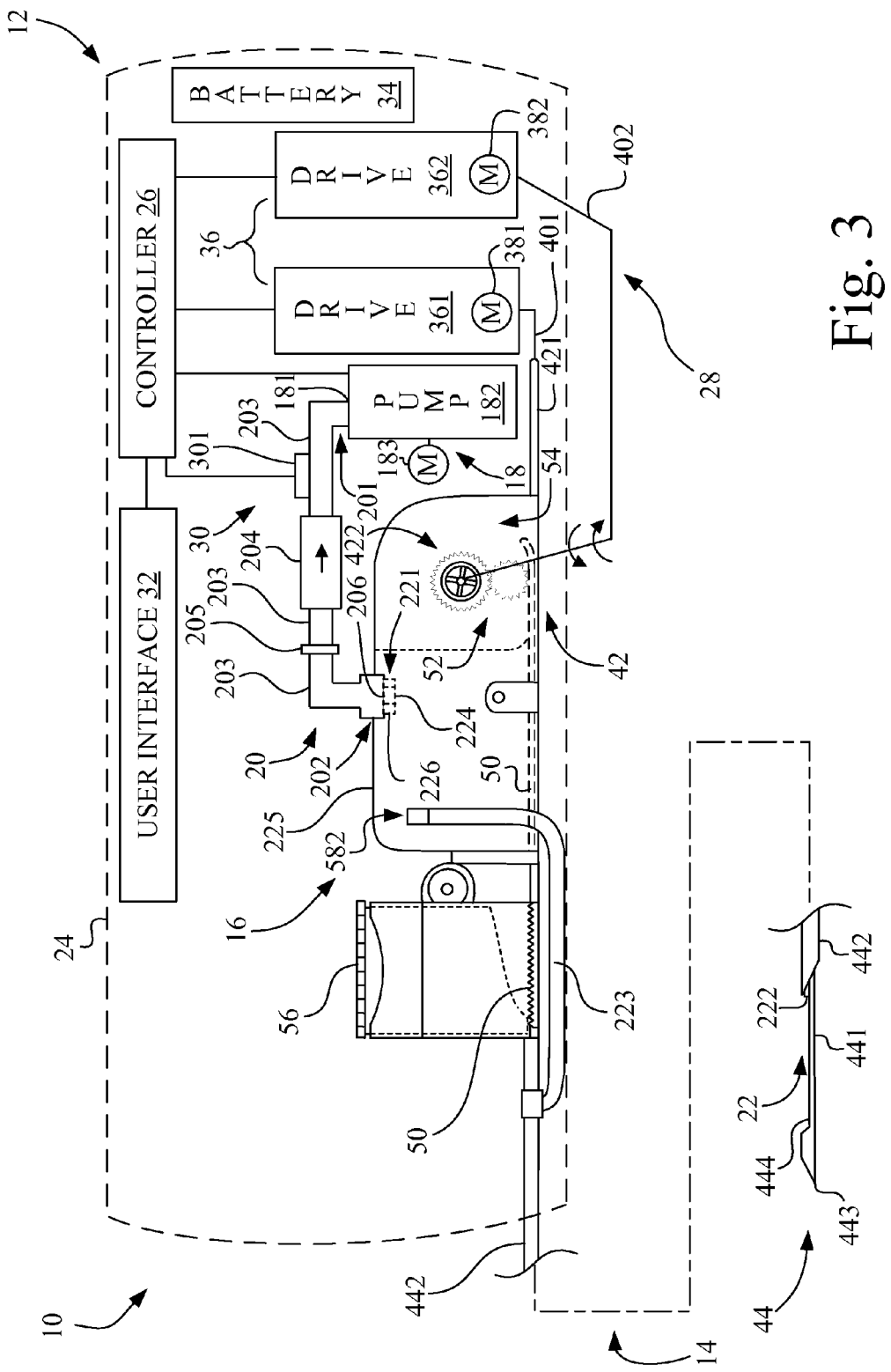
FIG. 3 is a schematic representation of the biopsy apparatus of FIG. 1.

Referring also to FIG. 3, driver assembly 12 and disposable biopsy probe assembly 14 collectively include a fluid management system 16 that includes a vacuum source 18, first vacuum path 20 and a second vacuum path 22. Vacuum source 18 and a first vacuum path 20 are permanently associated with driver assembly 12, and a second vacuum path 22 is permanently associated with disposable biopsy probe assembly 14, as more fully described below, to help facilitate the safe and effective collection of a biopsy tissue sample.

As used herein, the term "non-disposable" is used to refer to a device that is intended for use on multiple patients during the lifetime of the device, and the term "disposable" is used to refer to a device that is intended to be disposed of after use on a single patient. Also, the term "vacuum path" means a fluid passageway used to facilitate a vacuum between two points, the fluid passageway passing through one or more components, such as for example, one or more of tubing, conduits, couplers, and interposed devices. Also, the term "permanently associated" means a connection that is not intended for releasable attachment on a routine basis during the lifetime of the components. Thus, for example, driver assembly 12 including vacuum source 18 and first vacuum path 20 is reusable as a unit in its entirety, whereas disposable biopsy probe assembly 14 and second vacuum path 22 are disposable as a unit in its entirety.

Driver assembly 12 includes a housing 24 configured, and ergonomically designed, to be grasped by a user. Driver assembly 12 includes (contained within housing 24) vacuum source 18, first vacuum path 20, a controller 26, an electromechanical power source 28, and a vacuum monitoring mechanism 30. A user interface 32 is located to be mounted to, and externally accessible with respect to, housing 24.

Controller 26 is communicatively coupled to electromechanical power source 28, vacuum source 18, user interface 32, and vacuum monitoring mechanism 30. Controller 26 may include, for example, a microprocessor and associated memory for executing program instructions to perform functions associated with the retrieval of biopsy tissue samples, such as controlling one or more components of vacuum source 18 and electromechanical power source 28. Controller 26 also may execute program instructions to monitor one or more conditions and/or positions of components of biopsy apparatus 10, and to monitor the status of fluid management system 16 associated with driver assembly 12 and disposable probe assembly 14.

The user interface 32 includes control buttons 321 and visual indicators 322, with control buttons 321 providing user control over various functions of biopsy apparatus 10, and visual indicators 322 providing visual feedback of the status of one or more conditions and/or positions of components of biopsy apparatus 10.

The electromechanical power source 28 may include, for example, an electrical energy source, e.g., battery, 34 and an electrical drive assembly 36. Battery 34 may be, for example, a rechargeable battery. Battery 34 provides electrical power to all electrically powered components in biopsy device 10, and thus for simplicity in the drawings, such electrical couplings are not shown. For example, battery 34 is electrically coupled to vacuum source 18, controller 26, user interface 32 and electrical drive assembly 36.

In the present embodiment, electrical drive assembly 36 includes a first drive 361 and a second drive 362, each being respectively coupled to battery 34, and each of first drive 361 and second drive 362 respectively electrically and controllably coupled to user interface 32.

First drive 361 may include an electrical motor 381 and a motion transfer unit 401 (shown schematically by a line). Second drive 362 may include an electrical motor 382 and a motion transfer unit 402 (shown schematically by a line). Each electrical motor 381, 382 may be, for example, a direct current (DC) motor, stepper motor, etc. Motion transfer unit 401 of first drive 361 may be configured, for example, with a rotational-to-linear motion converter, such as a worm gear arrangement, rack and pinion arrangement, solenoid-slide arrangement, etc. Motion transfer unit 402 of second drive 362 may be configured to transmit rotary motion. Each of first drive 361 and second drive 362 may include one or more of a gear, gear train, belt/pulley arrangement, etc.

Vacuum source 18 is electrically coupled to battery 34, and has a vacuum source port 181 for establishing a vacuum. Vacuum source 18 is electrically and controllably coupled to user interface 32. Vacuum source 18 may further include, for example, a vacuum pump 182 driven by an electric motor 183. Vacuum pump 182 may be, for example, a peristaltic pump, a diaphragm pump, syringe-type pump, etc.

Figure 4A:
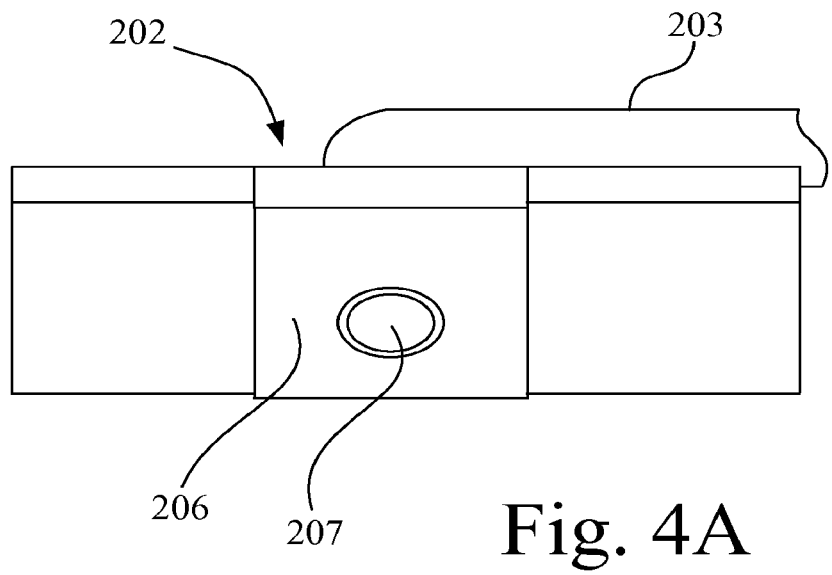
FIG. 4A is a perspective view of a vacuum seal element of the vacuum path of the driver assembly of FIG. 3.

First vacuum path 20 of driver assembly 12 is permanently associated with vacuum source 18. First vacuum path 20, also sometimes referred to as a non-disposable vacuum path, has a proximal end 201 and a distal end 202, and includes, for example, conduits 203, a first one-way valve 204, and a particulate filter 205. Proximal end 201 is fixedly coupled to vacuum source 18 in fluid communication therewith, e.g., is fixedly connected to vacuum source port 181 of vacuum source 18. Referring also to FIG. 4A, distal end 202 includes a first vacuum seal element 206. In the present embodiment, first vacuum seal element 206 is a planar abutment surface that surrounds a first passageway 207 of first vacuum path 20.

First one-way valve 204 is configured and arranged to permit a negative pressure fluid flow toward vacuum source 18 and to prevent a positive pressure fluid flow away from vacuum source 18 toward the distal end 202 of first vacuum path 20. The first one-way valve 204 may be, for example, a check-valve, such as a ball valve or reed valve, that opens with a fluid flow toward vacuum source 18, and closes in the case of a reverse (positive) flow away from vacuum source 18.

In the present embodiment, particulate filter 205 is located between vacuum source 18 and distal end 202 of first vacuum path 20. Particulate filter 205 may be, for example, a mesh screen formed from metal or plastic. However, it is contemplated that particulate filter 205 may be located in fluid management system 16 between vacuum source 18 and a vacuum receiving component of biopsy probe assembly 14.

The vacuum monitoring mechanism 30 is coupled to vacuum source 18 to shut off vacuum source 18 when a sensed vacuum level has fallen below a threshold level. Vacuum monitoring mechanism 30 may include, for example, a vacuum monitor and control program executing on controller 26, and a pressure sensor 301 coupled to controller 26, and in fluid communication with first vacuum path 20 for detecting a pressure in first vacuum path 20. If, for example, the vacuum flow level in first vacuum path 20 falls below a predetermined level, indicating a restriction in fluid management system 16, controller 26 may respond by shutting off vacuum source 18, e.g., turning off electric motor 183. Alternatively, controller 26 may monitor the current supplied to electric motor 183, and if the current exceeds a predetermined amount, indicating a restriction in fluid management system 16, controller 26 may respond by shutting off vacuum source 18, e.g., turning off electric motor 183.

The disposable biopsy probe assembly 14 is configured for releasable attachment to driver assembly 12. As used herein, the term "releasable attachment" means a configuration that facilitates an intended temporary connection followed by selective detachment involving a manipulation of disposable biopsy probe assembly 14 relative to driver assembly 12, without the need for tools.

The disposable biopsy probe assembly 14 includes a frame 141 to which a transmission device 42, a biopsy probe 44, and the second vacuum path 22 are mounted. Biopsy probe 44 is drivably coupled to transmission device 42, and transmission device 42 is drivably coupled to electromechanical power source 28 of driver assembly 12.

In the embodiment shown, transmission device 42 includes a first driven unit 421 and a second driven unit 422 that are drivably engaged with various components of biopsy probe 44. Also, first driven unit 421 is drivably engaged with first drive 361 of electrical drive assembly 36 of driver assembly 12. Second driven unit 422 is drivably engaged with second drive 362 of electrical drive assembly 36 of driver assembly 12.

In the embodiment shown (see, e.g., FIGS. 1-3), biopsy probe 44 includes a sample basket 441 and a cutter cannula 442. Sample basket 441 has a sharpened tip 443 to aid in puncturing tissue and has a sample notch 444 in the form of a recessed region for receiving a biopsy tissue sample.

In operation, cutter cannula 442 is linearly driven by first driven unit 421 to traverse over sample notch 444 of sample basket 441. For example, first driven unit 421 may be in the form of a linear slide that is drivably engaged with first drive 361 of driver assembly 12, which in turn drives cutter cannula 442 in a first direction 46 to expose sample notch 444 of sample basket 441, and drives cutter cannula 442 in a second direction 48 opposite to first direction 46 to sever tissue prolapsed into sample notch 444. Also, first driven unit 421 and second driven unit 422 may be configured to operate in unison to advance both sample basket 441 and cutter cannula 442 in unison in a piercing shot operation to aid in inserting biopsy probe 44 into fibrous tissue.

The second driven unit 422 may include a flexible toothed rack 50 and a gear train 52. Flexible toothed rack 50 is connected to sample basket 441, and gear train 52 is engaged with the teeth of flexible toothed rack 50. In operation, second drive 362 transfers rotary motion to gear train 52, and in turn gear train 52 engages flexible toothed rack 50 to move sample basket 441 linearly to transport the tissue captured in sample notch 444 out of the body of the patient. Flexible toothed rack 50 is received in a coiling unit 54 when retracting, thereby enabling substantial reduction in the overall device length of biopsy apparatus 10 as compared to a rigid capture system. The severed tissue sample is transported out of the body of the patient and into tissue sample chamber 56 (mounted to frame 141), which scoops the tissue sample out of sample notch 444.

In the present embodiment, the second vacuum path 22, also sometimes referred to as a disposable vacuum path 22, has a first end 221 and a second end 222, and includes for example, conduits 223, a second one-way valve 224, and a fluid management tank 225. The first end 221 is configured for removable attachment to the distal end 202 of the first vacuum path 20 of driver assembly 12. The second end 222 is coupled in fluid communication with sample basket 441, and more particularly, is coupled in fluid communication with sample notch 444 of sample basket 441.

Figure 4B:
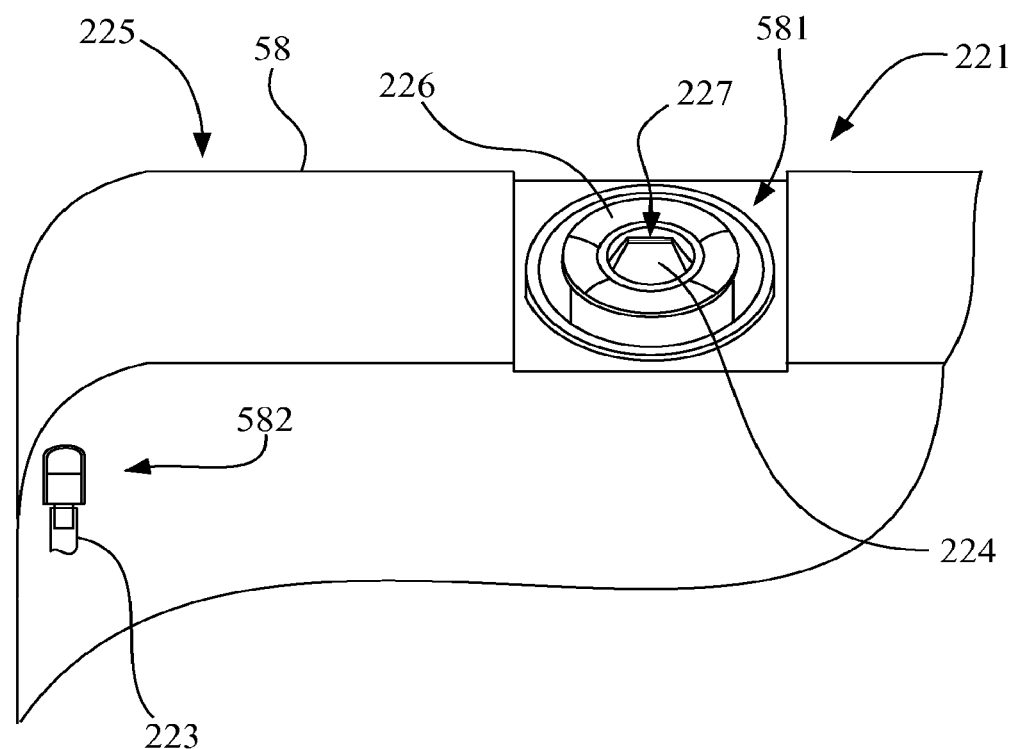
FIG. 4B is a perspective view of a vacuum seal element of the vacuum path of the disposable biopsy probe of FIG. 3.

Referring also to FIG. 4B, the first end 221 of the disposable vacuum path 22 includes a second vacuum seal element 226. The first vacuum seal element 206 of the driver assembly 12 contacts the second vacuum seal element 226 of the disposable biopsy probe assembly 14 in sealing engagement when the disposable biopsy probe assembly 14 is attached to driver assembly 12. The second vacuum seal element 226 is a compliant, e.g., rubber, annular member that surrounds a second passageway 227 of the second vacuum path 22.

The second one-way valve 224 configured and arranged to permit the negative pressure fluid flow from sample basket 441 toward the first end 221 of the second vacuum path 22, and to redundantly (in conjunction with first one-way valve 204 of driver assembly 12) prevent any positive pressure fluid flow in a direction from the first end 221 of the second vacuum path 22 toward sample basket 441. In other words, the second one-way valve 224 provides a redundant second level of protection in preventing any positive pressure from reaching sample notch 444 of sample basket 441. In the present embodiment, the second one-way valve 224 may be, for example, a duckbill valve, e.g., a reed-type valve, that opens with a fluid flow out the bill portion of the duckbill valve, and closes with a reverse flow. As shown, the second one-way valve 224 may be positioned within the second vacuum seal element 226 at first end 221 of second vacuum path 22.

Figure 5A:
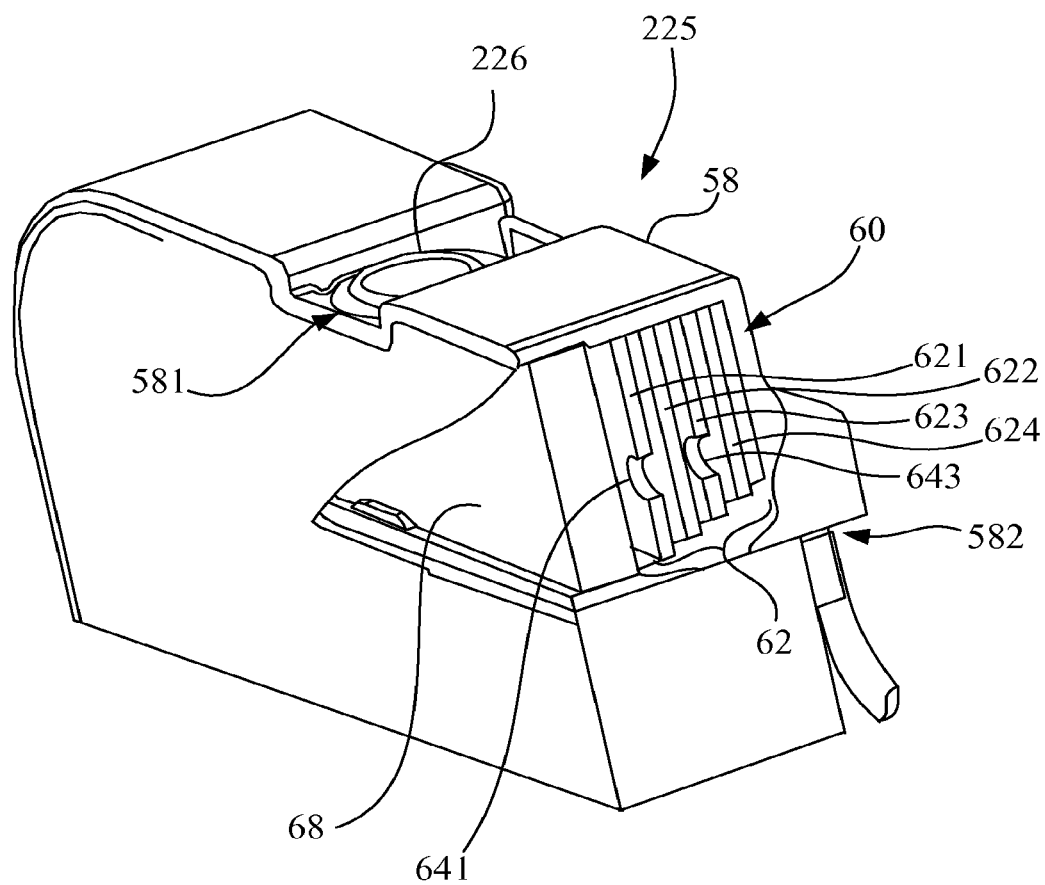
FIG. 5A is a perspective view of the fluid management tank of the disposable biopsy probe shown in FIGS. 2 and 3, with a portion broken away to expose a filter arrangement.

Referring also to FIG. 5A, fluid management tank 225 is fluidically interposed in the second vacuum path 22 between the first end 221 and the second end 222. Fluid management tank 225 includes a body 58 and a filter arrangement 60 contained within body 58 configured to prevent a flow of residual biopsy biological material, e.g., blood and particulate matter, from sample notch 444 of sample basket 441 to vacuum source 18 of driver assembly 12.

Body 58 of fluid management tank 225 has a first port 581 and a second port 582, with the second vacuum path 22 continuing between the first port 581 and the second port 582. The second port 582 of fluid management tank 225 is coupled to sample basket 441. Each of the second one-way valve 224 and the second vacuum seal element 226 of the second vacuum path 22 is coupled to the first port 581 of fluid management tank 225, and in the present embodiment, is mounted to an external surface of body 58 of fluid management tank 225.

Figure 5B:
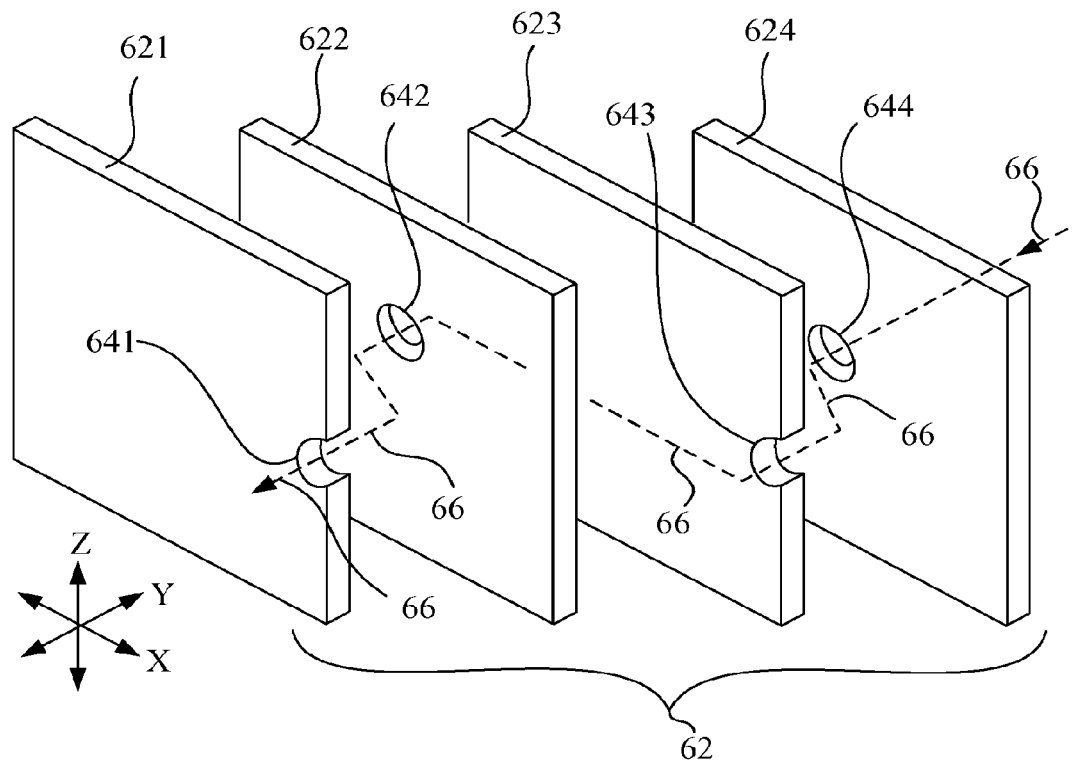
FIG. 5B is an exploded view of a plurality of fluid absorption layers of the filter arrangement of FIG. 5A.

As illustrated in FIGS. 5A and 5B, filter arrangement 60 includes a plurality of fluid absorption layers 62, individually identified as layers 621, 622, 623 and 624, arranged side by side, with each fluid absorption layer 621, 622, 623 and 624 being spaced apart from an adjacent fluid absorption layer e.g., 621 to 622, 622 to 623, 623, to 624. Each fluid absorption layer 621, 622, 623 and 624 has a respective through opening 641, 642, 643, 644, wherein adjacent through openings of through openings 641, 642, 643, 644 of the plurality of fluid absorption layers 62 are offset one to the next, e.g., in at least one of an X, Y, and Z direction, to form a tortuous open fluid passageway 66 through the plurality of fluid absorption layers 62. Each fluid absorption layer 621, 622, 623 and 624 may be, for example, a blotting paper.

Figure 5C:
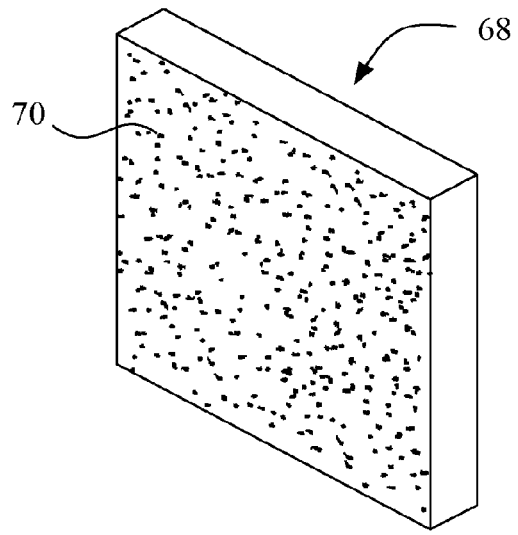
FIG. 5C is a perspective view of a porous filter element of the filter arrangement of FIG. 5A.

As illustrated in FIGS. 5A and 5C, filter arrangement 60 may further include a porous filter element 68 arranged to be fluidically in series with the plurality of fluid absorption layers 62 along the second vacuum path 22 that defines second passageway 227. The porous filter element 68 exhibits increased restriction to fluid flow as an increased number of pores 70 in the porous filter element 68 become clogged by residual biopsy biological material, such as blood and tissue particles. When a volume of the fluid flow through fluid management tank 225 has been reduced to a predetermined level, vacuum monitoring mechanism 30 senses the vacuum restriction, and controller 26 responds to shut off vacuum source 18.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A boipsy apparatus, comprising: (a) a driver assembly configured to be grasped by a user, including: an electromechanical power source; a vacuum source; and a first vacuum path permanently associated with said vacuum source, said first vacuum path having a proximal end and a distal end, said proximal end being fixedly coupled to said vacuum source in fluid communication therewith, said first vacuum path having a first one-way valve configured and arranged to permit a negative pressure fluid flow toward said vacuum source and to prevent a positive pressure fluid flow away from said vacuum source toward said distal end; and (b) a disposable biopsy probe assembly configured for releasable attachment to said driver assembly, said disposable biopsy probe assembly including: a transmission device configured to drive engagement with said electromechanical power source; a biopsy probe drivably coupled to said transmission device, said biopsy probe having a sample basket configured to receive a biopsy tissue sample; a second vacuum path having a first end and a second end, said first end being configured for removable attachment to said distal end of said first vacuum path and said second end being coupled in fluid communication with said sample basket, said second vacuum path having a second one-way valve configured and arranged to permit the negative pressure fluid flow from said sample basket and to redundantly prevent the positive pressure fluid flow from said first end of said second vacuum path toward said sample basket; and a fluid management tank fluidically interposed in said second vacuum path between said first end and said second end, said fluid management tank including body and a filter arrangement contained within the body configured to prevent a flow of residual biopsy biological material from said sample basket to said vacuum source.

2. The biopsy apparatus of claim 1, wherein said filter arrangement includes a plurality of fluid absorption layers arranged side by side, each fluid absorption layer being spaced apart from an adjacent fluid absorption layer, each fluid absorption layer having a respective through opening, wherein adjacent through openings of said plurality of fluid absorption layers are offset to form a tortuous open fluid passageway through said plurality of fluid absorption layers from one fluid absorption layer to a next fluid absorption layer.

3. The biopsy apparatus of claim 2, wherein said filter arrangement further includes a porous filter element arranged to be fluidically in series with said plurality of fluid absorption layers along said second vacuum path, wherein said porous filter element exhibits increased restriction to fluid flow as an increased number of pores in said porous filter element become clogged by residual biopsy biological material.

4. The biopsy apparatus of claim 3, comprising a vacuum monitoring mechanism coupled to said vacuum source to shut off said vacuum source when a volume of said fluid flow through said fluid management tank has been reduced to a predetermined level.

5. The biopsy apparatus of claim 4, wherein said vacuum monitoring mechanism includes a pressure sensor in fluid communication with said first vacuum path.

6. The biopsy apparatus of claim 1, wherein said filter arrangement includes a plurality of fluid absorption layers arranged side by side in a first direction, each fluid absorption layer being spaced apart from an adjacent fluid absorption layer in the first direction, said plurality of fluid absorption layers includes a first fluid absorption layer having a first through opening and a third fluid absorption layer having a third through opening, and wherein the first through opening and the third through opening are aligned along a fluid passageway in a direction transverse to the first direction, and wherein a second fluid absorption layer of the plurality of fluid absorption layers is interposed in the fluid passageway between the first through opening and the third through opening in the direction transverse to the first direction.

7. The biopsy apparatus of claim 1, comprising a particulate filter located between said vacuum source and said distal end of said first vacuum path.

8. The biopsy apparatus of claim 1, comprising:
a first vacuum seal element located at said distal end of said first vacuum path
a second vacuum seal element located at the first end of said second vacuum path, said first vacuum seal element contacting said second vacuum seal element in sealing engagement when said disposable biopsy probe assembly is attached to said driver assembly; and
said body of said fluid management tank having a first port and a second port, said second vacuum path continuing between said first port and said second port, said second port being coupled to said sample basket; and
each of said second one-way valve and said second vacuum seal being coupled to said first port and mounted to an external surface of said body of said fluid management tank.

* * * * *